US006080418A

United States Patent [19]

Sengupta et al.

[11] Patent Number: 6,080,418

[45] **Date of Patent: *Jun. 27, 2000**

[54] SUSPENSIONS OF MICROCAPSULES CONTAINING BIOLOGICALLY ACTIVE INGREDIENTS AND ADHESIVE MICROSPHERES

[75] Inventors: Ashok Sengupta, London; Kent E. Nielsen, Dorchester; Galina Barinshteyn, London, all of Canada; Kai Li, Arcadia, Calif.; John P. Banovetz, Minneapolis, Minn.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/834,971

[22] Filed: Apr. 7, 1997

[51] Int. Cl.[7] .......................... A01N 25/34; A01N 25/24; A61K 9/48; A61K 9/14

[52] U.S. Cl. .......................... 424/408; 424/404; 424/405; 424/407; 424/451; 424/455; 424/456; 424/489; 514/962

[58] Field of Search .................................... 424/489, 490, 424/497, 404, 405, 407, 408, 451, 456, 455; 514/962

[56] References Cited

U.S. PATENT DOCUMENTS

| | | | |
|---|---|---|---|
| 3,577,515 | 5/1971 | Vandegaer | 424/32 |
| 3,691,140 | 9/1972 | Silver . | |
| 3,917,711 | 11/1975 | Roelofs | 260/601 |
| 4,046,741 | 9/1977 | Scher . | |
| 4,107,292 | 8/1978 | Nemeth . | |
| 4,140,516 | 2/1979 | Scher | 71/88 |
| 4,417,916 | 11/1983 | Beestman | 71/93 |
| 4,436,719 | 3/1984 | Lindaberry . | |
| 4,487,759 | 12/1984 | Nesbitt | 424/32 |
| 4,520,142 | 5/1985 | Leinen | 523/205 |
| 4,557,755 | 12/1985 | Takahashi | 71/100 |
| 4,563,212 | 1/1986 | Becher | 71/118 |
| 4,632,829 | 12/1986 | Hedin | 424/84 |
| 4,670,246 | 6/1987 | Dahl et al. . | |
| 4,670,250 | 6/1987 | Baker | 424/419 |
| 5,045,569 | 9/1991 | Delgado . | |
| 5,260,071 | 11/1993 | Lemelson . | |
| 5,332,584 | 7/1994 | Scher | 424/408 |
| 5,508,313 | 4/1996 | Delgado et al. . | |

FOREIGN PATENT DOCUMENTS

| | | |
|---|---|---|
| 1044134 | 3/1976 | Canada . |
| 1179682 | 3/1981 | Canada . |
| 371 635 | 6/1990 | European Pat. Off. . |
| 611253 | 2/1994 | European Pat. Off. . |
| 1371179 | 2/1973 | United Kingdom . |
| WO 9213924 | 8/1992 | WIPO . |
| WO 96/33611 | 10/1996 | WIPO . |

*Primary Examiner*—Thurman K. Page
*Assistant Examiner*—Brian K. Seidleck
*Attorney, Agent, or Firm*—Dale A. Bjorkman

[57] ABSTRACT

A composition comprising two suspensions: A) an aqueous suspension of microcapsules containing biologically active materials and B) an adhesive suspension of adhesive microspheres. The composition is useful for adhering microencapsulated biologically active material onto an intended substrate.

15 Claims, No Drawings

SUSPENSIONS OF MICROCAPSULES CONTAINING BIOLOGICALLY ACTIVE INGREDIENTS AND ADHESIVE MICROSPHERES

FIELD OF THE INVENTION

The present invention relates to suspensions of adherent capsules containing biologically active ingredients.

BACKGROUND OF THE INVENTION

It is known to encapsulate various materials, often by interfacial polycondensation. For instance, U.S. Pat. No. 3,577,515 speaks of capsules containing dyes, inks, chemical reagents, pharmaceuticals, flavoring material, pesticides, herbicides, peroxides and indeed anything which can be dissolved, suspended or otherwise constituted in or as a liquid enclosed by the capsule. United Kingdom Patent No. 1,371,179 discloses the preparation of polyurea capsules for containing dyes, inks, chemical reagents, pharmaceuticals, flavoring materials, fungicides, bactericides and pesticides such as herbicides and insecticides. U.S. Pat. Nos. 4,046,741; 4,140,516; 4,417,916; 4,563,212 and European Patent No. 611,253 are concerned with encapsulation of various materials. Canadian Patent No. 1,044,134 is concerned with encapsulation of insecticides, particularly pyrethroids. Canadian Patent No. 1,179,682 is concerned with encapsulation of pheromones. A pending U.S. patent application Ser. No. 08/834,937, filed on even date with this application, is also concerned with encapsulating various materials, including biologically active materials such as pheromones.

The above-mentioned patents make use of various forms of interfacial polycondensation, particularly the formation of capsules having polyurea and/or polyurethane/polyurea shell walls. The capsules made by the various processes are said to range in diameter from about 1 micron to about 2 mm, but most fall towards the lower end of this range, i.e., from about 250 microns, or even 100 microns, down to about 1 micron.

SUMMARY OF THE INVENTION

An aqueous suspension of microcapsules containing a biologically active material, which suspension further comprises an adhesive material in an amount effective to enable said microcapsules to adhere to an intended substrate.

DESCRIPTION OF THE PREFERRED EMBODIMENTS

For purposes of the present invention, the term "biologically active" means materials that affect the life processes of organisms. Materials that are biologically active include herbicides, pesticides, pharmaceuticals, and semiochemicals, including naturally and artificially produced pheromones.

Microcapsules containing such biologically active ingredients and additionally containing an adhesive material advantageously may be applied by spraying. This is particularly advantageous in the fields of forestry, agriculture and horticulture, where aerial spraying is preferred as a means of application. The sprayed capsules are applied to foliage, to which continued contact is desired. For instance, insecticides and pheromones should remain on the foliage if they are to display maximum effect. In the absence of the adhesive material described herein, the microcapsules may be blown or washed off of the foliage by wind and rain. It is necessary that any treatment to render the capsules adherent should not be at the expense of other valuable properties. For instance, for spraying for use in forestry, agriculture or horticulture the capsules are ideally discrete particles that will remain in suspension in water, usually with a suspending agent. Adherent properties imparted to the capsules should not have the result that the capsules aggregate together in aqueous suspension. Such aggregation would of course render the capsules unsuitable for spraying and defeat the whole purpose of the capsules. Furthermore, any material used to impart adherent properties should not affect the integrity of the particles; it should not dissolve or weaken the shell of the capsule.

The present compositions are aqueous suspensions, which provides a significant advantage in use. Other compositions that deliver encapsulated insecticides and herbicidess are solvent based, which is a significant disadvantage because such solutions release volatile organic compounds (VOCs) to the environment. For purposes of the present invention, a volatile organic compound (VOC) is any volatile organic material having a vapor pressure at 20° C. greater than 0.1 Torr (mm Hg) that is not an active ingredient (e.g. an insecticide, herbicides or the like). More preferably, Volatile Organic Compounds may be defined as having a vapor pressure at 20° C. greater than 0.02 Torr that is not an active ingredient. Because aqueous suspensions of the present invention need not contain any appreciable amount of these undesirable VOCs, the overall composition is significantly more environmentally friendly. Preferred compositions of the present invention contain no more than 5% VOC by weight, and most preferably contain no more than 2% VOC by weight. Jurisdictions such as Los Angeles and so forth that have a significant air pollution problem would find the present aqueous suspensions to be highly preferred due to their low pollution effect on the environment.

While adhesive materials are sometimes used in agriculture today to help herbicides and insecticides stick to organic substrates, until now the latex has been used to a limited extent only with unencapsulated chemicals. Surprisingly, it has been found that incorporation of adhesive with microencapsulated biologically active materials results in a composition that is still sprayable from a conventional spraying apparatus. Contrary to expectations, it has been found that the sticky microcapsules of the instant composition do not agglomerate at the spray orifice or in the storage vessel. During application, the adhesive latex associates with the microcapsules and therefore does not entirely coat the surface of the target substrates. Because the adhesive is soluble or dispersible in water, the composition has a limited but effective lifetime on the target substrate before weather eventually removes the material from the substrate.

The adhesive latex used in the present composition may be any suitable water-dispersible adhesive available in the art. In the agricultural business, such latex compositions are often called stickers or spreaders. Stickers are used to help non-encapsulated agriculture chemicals adhere to plants. Spreaders are used to help disperse non-encapsulated agriculture chemicals on application. Preferred adhesives are acrylate-based adhesives. One suitable latex is available from Rohm & Haas under the trade-mark Companion. Another is available from Deerpoint Industries under the trade-mark DPI S-100 (a proprietary sticker/spreader). Examples of such adhesives are polymers made from the "soft" monomers such as n-butyl acrylate, isooctyl acrylate, or the like, or copolymers made from a soft component, such as isobutylene, n-butyl acrylate, isooctyl acrylate, ethyl hexyl acrylate, or the like; and a polar monomer such as acrylic acid, acrylonitrile, acrylamide, methacrylic acid, methyl methacrylate or the like. Non-spherical polyacrylate adhesives are commercially available, for example, as the Rohm and Haas Rhoplex™ line of adhesives. Preferably, the non-spherical polyacrylate adhesive is present in an amount of about 10–35% by weight of the total suspension.

It further has surprisingly been found that tacky microspheres of adhesive may be used to adhere biologically active material containing microcapsules to an intended substrate. The tacky microspheres have sufficient adhesive properties to provide the desired adhesive function, and there is no danger of completely coating the microcapsule and possibly inhibiting the release characteristics of the capsule. Surprisingly, the combination of biologically active material containing microcapsules and tacky microspheres may be applied without the need to modify the orifices of conventional sprayers with minimal clogging or plugging problems.

Preferably, the adhesive material is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569. Other suitable adhesives are the tacky microspheres having pendant hydrophilic polymeric or oligomeric moieties that are disclosed in U.S. Pat. No. 5,508,313.

Alternatively, the adhesive comprises between about 60–100% by weight of hollow, polymeric, acrylate, inherently tacky, infusible, solvent-insoluble, solvent-dispersible, elastomeric pressure-sensitive adhesive microspheres having a diameter of at least 1 micrometer, and between about 0–40% by weight of a non-spherical polyacrylate adhesive. The hollow microspheres are made in accordance with the teaching of European Patent Application 371,635.

Biologically active materials are preferably selected from pharmaceuticals, fungicides, bactericides and pesticides such as herbicides and insecticides. Particularly preferred biologically active materials are the pyrethroids, pheromones and other such semiochemicals, whether naturally produced or artificially synthesized.

The microcapsules may be any of the microcapsules suitable for encapsulating biologically active materials, including polyurea, polyurethane, melamine/urea, gelatin microcapsules or the like. The microcapsules containing the biologically active material preferably are provided in a size in the range of from 1 micron to 2 mm.

Also provided is a process for preparing an aqueous suspension of adherent microcapsules. It has surprisingly been discovered that careful mixing of the ingredients of compositions of the present invention under basic conditions can be particularly beneficial for avoiding the formation of a coagulum that would be impossible to apply using conventional spraying equipment. The process comprises admixing A) an aqueous suspension of microcapsules having a pH either greater than or less than 7 with B) an aqueous suspension of adhesive having a pH either greater than or less than 7, such that the pH of A) and B) are both greater than 7 or less than 7. The adhesive suspension is selected from the group consisting of adherent microspheres, non-spherical aqueous latex adhesive or a combination of adherent microspheres and non-spherical aqueous latex adhesive. Most preferably, the mixing takes place at a pH between about 8 and about 9. Any base can be used to control the pH, for example alkali metal or alkaline earth metal hydroxides or carbonates, but the simplest and preferred is ammonia in aqueous solution.

Typically, the aqueous suspension A) of microcapsules of the present invention may contain from about 5 to 40 percent microcapsules by weight, and preferably from about 5 to 25 percent microcapsules by weight before mixing with the adhesive composition. Typically, the aqueous suspension B) of adhesive may contain from about 5 to 60 percent of the adhesive by weight, preferably about 25 to 40 percent of the adhesive by weight before mixing with the microcapsule composition. Suitably about 10 to 30 parts by weight of aqueous suspension of adhesive microspheres (composition B) is added to about 90 to 70 parts by weight of aqueous suspension of microcapsules (composition A), to form a suspension of the invention. If a latex of non-spherical adhesive material is used the amount is again suitably from about 10 to 30 parts by weight, added to about 90 to 70 parts by weight of the suspension of microcapsules.

The aqueous suspension of the microcapsules and the aqueous suspension of the adhesive microspheres, or the latex containing adhesive material, should be admixed slowly and carefully, with stirring, to avoid breaking the suspension. The admixture is suitably done at room temperature.

As noted above, the compositions of the present invention are specially suited to be delivered to an intended substrate in an easy and economic manner. Specifically, the compositions of the present invention are readily and effectively delivered to organic substrates, such as foliage, crops and weeds. The unique formulation enables microcapsules containing a biologically active ingredient to adhere to these organic materials without unduly coating the substrate and unintentionally interfering with their life processes. Similarly, compositions of the present invention can readily be applied to skin and hair of non-human as well as human subjects in need of treatment. Further, the present compositions can be applied to non-organic substrates, such as buildings, pavements, ground and the like in an efficient and effective manner with excellent retention of the active ingredient to the intended substrate.

Surprisingly, it has been found that an aqueous suspension of microcapsules and adhesive material may economically be applied to an intended substrate through a spray device in the form of an aerosol. This method of application may advantageously be employed for microcapsules containing any fill material, but is particularly desirable for microcapsules that contain a biologically active material. In such cases, the intended substrate is preferably foliage, crops or weeds. Most preferably, the adhesive material is an aqueous suspension of adhesive microspheres. Such microspheres surprisingly provide excellent adhesion to the intended substrate and do not coat the microcapsules or inhibit release of the encapsulated contents thereof.

The disclosures of U.S. Pat. Nos. 3,691,140; 5,045,569; and 5,508,313 and European Patent Application 371,365 and the above-mentioned patent application Ser. No. (08/834,937) are incorporated herein by reference.

The invention is illustrated in the following examples.

EXAMPLE 1

An aqueous suspension of adhesive microspheres (20 g, as described in U.S. Pat. No. 5,508,313, example 2 having a ratio of IOA:AA:Carbowax of 97:2:1) was neutralized with NH40H (8 g in 20 g water). An aqueous suspension of microcapsules of a pheromone, E-11-tetradecen-1-yl acetate encapsulated in a polyurea shell (50 g) and rhamsam gum suspending agent were added, with stirring. A good suspension of adherent microcapsules was obtained.

In a comparative test, adhesive microspheres (20 g as described above) were mixed with 20 g water. An aqueous suspension of microcapsules of E-11-tetradecen-1-yl acetate in a polyurea shell (50 g) and a rhamsun gum suspending agent was added, with agitation. The components coagulated and, despite dilution with a further 80 g of water there was obtained a useless coagulum.

What is claimed is:

1. An aqueous suspension of microcapsules containing a biologically active material, which suspension further comprises an aqueous adhesive suspension of tacky adhesive microspheres in an amount effective to enable said microcapsules to adhere to an intended substrate, wherein said microspheres are acrylate- or methacrylate-based infusible, solvent dispersible, solvent insoluble inherently tacky, elastomeric copolymeric microspheres, said microcapsules are composed of an encapsulated biologically active material in a shell selected from the group consisting of polyurea, polyurethane, melamine/urea and gelatin; and said aqueous suspension of tacky adhesive microspheres contains from about 5 to 60 percent of said adhesive microspheres by weight before mixing with said suspension of microcapsules.

2. A suspension as claimed in claim 1 wherein the adhesive microspheres are hollow.

3. A suspension as claimed in claim 1 wherein the biologically active material is a pharmaceutical.

4. A suspension as claimed in claim 1 wherein the biologically active material is selected from the group consisting of fungicides and bactericides.

5. A suspension as claimed in claim 1 wherein the biologically active material is a pesticide.

6. A suspension as claimed in claim 4 wherein the biologically active material is selected from the group consisting of herbicides and insecticides.

7. A suspension as claimed in claim 1 wherein the biologically active material is selected from the group consisting of pyrethroids and pheromones.

8. A suspension as claimed in claim 1 wherein the microcapsules are provided in a size in the range of from 1 micron to 2 mm.

9. A process for preparing an aqueous suspension of microcapsules and tacky adhesive microspheres, which process comprises admixing an aqueous suspension A) of microcapsules having a pH greater than about 7, wherein said microcapsules are composed of an encapsulated biologically active material in a shell selected from the group consisting of polyurea, polyurethane, melamine/urea and gelatin; with an aqueous suspension B) of tacky adhesive microspheres having a pH greater than about 7, wherein said microspheres are acrylate- or methacrylate-based infusible, solvent dispersible, solvent insoluble, elastomeric copolymeric microspheres; and wherein said aqueous suspension B) of tacky adhesive microspheres contains about 5 to 60 percent of said adhesive microspheres by weight before mixing with said suspension A) of microcapsules.

10. A process according to claim 9 wherein aqueous ammonia is used to provide the pH greater than about 7.

11. A process according to claim 9 wherein the pH is between about 8 and about 9.

12. A process for preparing an aqueous suspension of microcapsules and tacky adhesive microspheres, which process comprises admixing an aqueous suspension A) of microcapsules having a pH less than about 7, wherein said microcapsules are composed of an encapsulated biologically active material in a shell selected from the group consisting of polyurea, polyurethane, melamine/urea and gelatin; with an aqueous suspension B) of tacky adhesive microspheres having a pH less than about 7, wherein said microspheres are acrylate- or methacrylate-based infusible, solvent dispersible, solvent insoluble, elastomeric copolymeric microspheres; and wherein said aqueous suspension B) of tacky adhesive microspheres contains about 5 to 60 percent of said adhesive microspheres by weight before mixing with said suspension A) of microcapsules.

13. A process according to claim 9, wherein the aqueous suspension B) of tacky adhesive microspheres contains from about 25 to 40 percent of the adhesive by weight before mixing with the microcapsule suspension A).

14. A process according to claim 9, wherein about 10 to 30 parts by weight of aqueous suspension B) of tacky adhesive microspheres is added to about 90 to 70 parts by weight of aqueous suspension A) of microcapsules.

15. A method for applying microcapsules to an intended substrate, comprising a) preparing an aqueous suspension A) of microcapsules, which suspension further comprises a suspension B) of tacky adhesive microspheres in an amount effective to enable said microcapsules to adhere to an intended substrate, wherein said microcapsules are composed of an encapsulated biologically active material in a shell selected from the group consisting of polyurea, polyurethane, melamine/urea and gelatin; with an aqueous suspension B) of tacky adhesive microspheres having a pH greater than about 7, wherein said microspheres are acrylate- or methacrylate-based infusible, solvent dispersible, solvent insoluble, elastomeric copolymeric microspheres; and wherein said aqueous suspension B) of tacky adhesive microspheres contains about 5 to 60 percent of said adhesive microspheres by weight before mixing with said suspension A) of microcapsules; and b) delivering said suspension to an intended substrate through a spray device in the form of an aerosol.

* * * * *